United States Patent [19]
Corma Canos et al.

[11] Patent Number: 5,783,167
[45] Date of Patent: Jul. 21, 1998

[54] STRUCTURE MATERIAL OF THE ZEOLITE TYPE WITH ULTRALARGE PORES AND A LATTICE COMPRISED OF SILICONE AND TITANIUM OXIDES: ITS SYNTHESIS AND UTILIZATION FOR THE SELECTIVE OXIDATION OF ORGANIC PRODUCTS

[75] Inventors: Avelino Corma Canos; Teresa Navarro Villalba, both of Valencia; Joaquin Perez Pariente, Madrid, all of Spain

[73] Assignees: Consejo Superior Investigaciones Cientificas, Madrid; Universidad Politecnica Valencia, Valencia, both of Spain

[21] Appl. No.: 413,867

[22] Filed: Feb. 15, 1995

Related U.S. Application Data

[63] Continuation of PCT/ES94/00059 Jun. 10, 1994.

[30] Foreign Application Priority Data

Jun. 15, 1993 [ES] Spain ..................... 9301327

[51] Int. Cl.$^6$ ............... C01B 33/20; B01J 29/04
[52] U.S. Cl. ............ 423/701; 423/702; 423/703; 423/704; 423/705; 423/706
[58] Field of Search ................... 423/701, 702, 423/703, 704, 705, 706

[56] References Cited

U.S. PATENT DOCUMENTS

| | | |
|---|---|---|
| 4,410,501 | 10/1983 | Taramsso et al. |
| 5,064,629 | 11/1991 | Asaoka . |
| 5,098,684 | 3/1992 | Kresge et al. |
| 5,102,643 | 4/1992 | Kresge et al. |
| 5,174,888 | 12/1992 | Kresge et al. |
| 5,196,633 | 3/1993 | Kresge et al. |
| 5,198,203 | 3/1993 | Kresge et al. |
| 5,246,689 | 9/1993 | Beck et al. |

FOREIGN PATENT DOCUMENTS

| | | |
|---|---|---|
| WO 91/18833 | 12/1991 | WIPO . |
| WO 93/02013 | 2/1993 | WIPO . |
| 9429022 | 12/1994 | WIPO . |

OTHER PUBLICATIONS

Titanium–Containing Mesoporous Molecular Sieves For Catalytic Oxidation of Aromtic Compounds (Peter T. Tanev, Malama Chibwe & Thomas J. Pinnavala, Nature vol. 368, Mar. 24, 1994).

*Primary Examiner*—Mark L. Bell
*Assistant Examiner*—Louis M. Troilo
*Attorney, Agent, or Firm*—Darby & Darby

[57] ABSTRACT

The invention relates to a material comprised of silicotitanates having a crystalline structure similar to MCM-41 zeolites, said material being characterized in that it contains in its lattice atoms of titanium and channels in its porous structure whose average sizes exceed 10 Å, making possible its utilization in catalytic reactions wherein are involved large organic molecules, such as the oxidation of olefins to epoxides and glycols, alcohols to cetones, thio-ethers to sulfoxides and sulfones, and phenol to catechol and hydroquinone, and if Al is introduced into the structure it is then possible to prepare bifunctional catalysts "oxidant-acid/base." In order to obtain such product, and aqueous solution is used which contains the ion $NR_1N_2N_3N_4^+$ as well as another aqueous solution which contains tetramethyl ammonium hydroxide and a silica source (e.g. aerosil®). After homogenization, more silica is added, as is the Ti source [e.g. $Ti(C_2OH_5)_4$]. The resultant gel is heated in an autoclave at a temperature between 80° and 200° C. It is used for catalytic oxidation.

29 Claims, 3 Drawing Sheets

STRUCTURE MATERIAL OF THE ZEOLITE TYPE WITH ULTRALARGE PORES AND A LATTICE COMPRISED OF SILICONE AND TITANIUM OXIDES: ITS SYNTHESIS AND UTILIZATION FOR THE SELECTIVE OXIDATION OF ORGANIC PRODUCTS

This is a continuation of international application Ser. No. PCT/ES94/00059, filed Jun. 10, 1994.

TECHNICAL FIELD

Zeotypes, catalytic oxidation

PRIOR ART

It has been recently revealed that silicotitanate and silicoaluminate isomorphs with zeolites with MFI and MEL structures (patent U.S. Pat. No. 4,410,501) are active for selective oxidation with $H_2O_2$ of olefins, alcohols, as well as for hydroxylation of aromatic compounds, amoxydation of ketones in the presence of $NH_3$ and oxidation of alkanes to alcohols and ketones (U. Romano, A. Espósito, F. Maspero, C. Neri and M. G. Clerici, *Stud. Surf. Sci. Catal.* 55, 33 (1990).) These materials are formed by a bidirectional system of channels with a pore diameter in the neighborhood of 5.5 Å, which imposes geometric restrictions and limits the size of the molecules to be oxidized. In these silicotitanates, it has been proposed that the active centers be Ti=O species bonded to the lattice.

The possibilities of these materials as oxidation catalysts have been increased, as a silicoaluminotitanate isomorph to Beta zeolite, which has a three-dimensional system of channels whose diameter is 7.3×6.0 Å (polytype A), or 7.3×6.8 Å (polytype B) for the channels parallel to the crystalographic axes a and b and 5.6×5.6 Å (polytype A) or 5.5×5.5 (polytype B) for the channels parallel to axis C has been synthesized (M. A. Camblor) A. Corma, J. Perez-Pariente, Spanish patent P9101798; M. A. Camblor, A. Corma, J. Pérez-Pariente, *J. Chem. Soc. Chemical Comm.* (1992) 557.) This Beta-Ti allows the oxidation of larger sized molecules than Titanium silicalite, but even so its possibilities are limited to molecules of a size, which is at the most the diameter of the channels.

BRIEF SUMMARY OF THE INVENTION

There is no doubt that in the field of fine chemistry, it is necessary to oxidize molecules with an effective diameter larger than 6.5 Å, which would have diffusional limitations, even in the Beta-Ti. Hence, it turns out to be of great interest to synthesize molecular sieves with a pore diameter larger than 6.5 Å and with Ti in the lattice. These materials could act as selective oxidation catalysts of molecules of interest in the field of organic chemistry.

The material to which the present invention refers has a MCM-41 type structure like the one described in patents U.S. Pat. No. 5,098,684, U.S. Pat. No. 5,102,643 and U.S. Pat. No. 5,108,725, but it has in its lattice titanium atoms (like patent ES 9101798) and, also has channels with an average dimension larger than 10 Å. The presence of Ti=O bonds in the material converts it into a catalyst suitable for selective oxidatons like the ones mentioned in patent ES 9101798, at the same time that the large diameter of the channels allows the access to the active centers of relatively voluminous organic molecules.

DETAILED DESCRIPTION OF THE INVENTION

On the one hand, the present invention refers to a porous material of a MCM-41 zeolite type stature and whose lattice is basically comprised of Si, Ti and optionally Al oxides; and on the other hand the way to prepare it and to its use as a catalyst in oxidation reactions of organic compounds.

DESCRIPTION OF THE MATERIAL

The composition of this material in its anhydrous form once roasted responds to the formula:

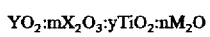

$$YO_2:mX_2O_3:yTiO_2:nM_2O$$

containing

- A $YO_2$ oxide, wherein Y represents one or several cations with a valence of 4, preferably Si and Ge.
- An $X_2O_3$ oxide, wherein X represents one or several cations with a valance of 3, preferably Al, Ga and B.
- A titanium oxide, $TiO_2$.
- An $M_2O$ oxide, wherein M represents one or several cations, preferably $Na^+$, $K^+$, or H characterized in that they may be easily changed by ionic exchange.

The range of molar proportions of these oxides is the following:

- The proportion $X_{23}/YO_2$ is $\leq 0.1$.
- The proportion $TiO_2/YO_2$ is between $10^{-4}$ and 0.2.
- The proportion $M_2O/YO_2$ is $\leq 0.1$.

A distinctive characteristic of this material, aside from its chemical composition, is that of having:

- Xray diffraction diagrams in which there is at least one diffraction peak corresponding to a spaced value d>18Å.
- A porosity larger than 0.2 $cm^3 \cdot g^{-1}$ and a pore distribution comprised between 5 and 200 Å, with an average diameter larger than 10 Å.
- The presence of an intense band at 960±5 $cm^{-1}$ in its infrared spectrum that reveals the inclusion of titanium in the lattice.

Preparation of the Product

In order to obtain the product whose characteristics have just been enumerated, the following operative process may be used:

One begins with an aqueous or alkaline alcohol solution of a quaternary ammonium salt $NR_1R_2R_3R_4^+$, wherein $R_2$, $R_3$ and $R_4$ may be the same or different and they represent organic groups with a chain length between 1 and 6 carbon atoms, the preferred composition thereof being $R_2=R_3=R_4=CH_3$, R represents an organic group that contains carbon or hydrogen, saturated or unsaturated, preferably one linear or branched aliphatic chain, the number of C atoms of this chain may vary between 2 and 36, those organic groups that contain between 10 and 18 carbon atoms being preferred; non-restrictive examples of this structuring agent are hexadecyltrimethylammonium, ddecyltrimethylammonium, benzyltrimethylammonium, dimethyl-didodecylammonium, hexadecylpyridinium and hexadecyltrimetylphosphonium cations. The solvent is between 5 and 50%, preferably 25% and the molar proportion of anion to $OH^-$ is between 0 and 20, preferably ½ Å.

In the event that the solvent used is an alcohol, instead of water, the alcohol or alcohols may have a linear or branched chain, the number of carbon atoms in the chainvarying between 1 and 16. An hydroalcohol solution can also be used when water-soluble alcohols are used.

Independently another aqueous solution containing between 10 and 50% tetramethylammonium hydroxide and between 5 and 20 % SiO₂ is prepared. Both solutions are mixed in the proportion of 0 to 0.5 g of the second one per g of the first one and after homogenization thereof by stirring the tetravalent element, preferably SiO₂, dissolves, in the proportion of 0.18 to 1.8 mols per liter of solution, and the titanium source (preferably tetraethylalkoxide, Ti(CH₂H₅O)₄) is added so that the TiO₂/SiO₂ ratio in the mixture is between $10^{-4}$ and 0.2. Optionally, instead of titanium, aluminum in the form of chloride, AlCl₃ can be added up to a maximum proportion of Al₂O₃/SiO₂ in the mixture 0.1.

In the event that one desires the material to contain alkaline ions, a solution of a Na⁺or K⁺salt, such as NaCl or KCl for example, can also be added to the previous mixture.

As a silica source amorphous silica or tetraalkoxysilanes, such as tetraethyl orthosilicate is preferably used. Preferably Ti alkoxides, such as isopropoxide or Ti tetraethoxide or a Ti halide preferably chloride are used as a Ti source. If one wishes to include Al or another trivalent cation, preferably sodium aluminate, or an Al salt, or one of the corresponding trivalent metal, preferably nitrate, can be used as the source of the same.

Table I shows the proportions, regarding the SiO₂ content of the different components of the mixture to be gelled.

TABLE I

Proportion of components in the mixture

| Proportion | Maximum limits | Recommended limits |
|---|---|---|
| TiO₂/SiO₂ | $10^{-4}$–0.2 | $10^{-4}$–0,17 |
| Al₂O₃/SiO₂ | 0–0.1 | 0–0.1 |
| OH⁻/SiO₂ | <10 | 0,1–5 |
| Solvente/SiO₂ | 1–1500 | 10–100 |
| M⁺/SiO₂ | 0–0,1 | 0–0,05 |
| (TMA)₂O/SiO₂ | <0,5 | <0,3 |
| (NR₁R₂R₃R₄)₂O/SiO₂ | 0,01–2 | 0,02–0,5 | wherein M⁺ is an alkaline cation, preferably Na⁺or K⁺or a mixture of both that can be added preferably as a hydroxide or as a salt (preferably choride) or as a sodium aluminate or as a mixture of both.

Once the mixture has gelled it is subjected to some hydrothermal conditions between 60° and 2000° C. and preferably between 80° and 180° C., for a period between 2 and 180 hours and preferably between 5 and 140 hours. After this operation, a crystalline product that is separated by filtration is obtained.

Roasting in air or in N₂ of the crystalline product obtained, at temperatures higher than 400° C., caused combustion or decomposition respectively of the organic material that is contained.

Utilization of the material

The material obtained by this process, which we will call MCM-41-Ti type zeotype, is active in reactions of selective oxidation of organic compounds, in which the oxidizing agent can be a peroxide or an organic or inorganic hydroperoxide or hydrogen peroxide, which can be added directly or generated "in situ." Examples of reactions in which its activity has been tested are oxidations of cycloalkanes to the corresponding alcohols and ketones, and especially of cyclohexane, cyclooctane, cyclodecane; of phenol to catechol and hydroquinone, of alkenes to epoxides, of alcohols to ketones and of thioethers to sulfoxides and sulfanes. Likewise, if Al is introduced into the MCM-41-Ti, this can catalyze the dehydration of glycols to alkenes and the dimerization of alcohols.

In the event that it contains Al, by means of ionic exchange, MCM-41-Ti in acid form (pronic) or base form (with alkaline cations) can be obtained whereby it is possible to prepare bifunctional catalysts that contain the oxidizing function and an acid-base function.

EXAMPLES

Example 1

Preparation of MCM-41-Ti 100 gr of a solution that contains 9.8% cetyltrimethylammonium hydroxide (CTMAOH) and 15% cetyltrimethylammonium bromide are prepared. Another solution comprised of 1.96 grams of SiO₂ (Aerosil 200© of Degussa®) dissolved in 17.66 g. of a tetramethylammonium hydroxide solution (TMA) 25% in water is added to this solution, while stirring is maintained. After achieving perfect homogenization, silica (Aerosil©) and the Ti source (Ti (C₂H₅O)₄) are added, maintaining stirring, in amounts so that the following molar ratios in the synthesis gel are obtained:

$$\frac{Si}{Ti} = 19; \frac{(CTMA)_2O}{(TMA)_2O} = 0.563; \frac{(TMA)_2O}{SiO_2} = 0.155 = \frac{H_2O}{(TMA)_2O} = 169$$

The prepared gel was introduced in a static autoclave heated to 135° C., for 22 hours.

Afterwards, it is filtered, washed to a pH≦10 and after drying it at room temperature, it is treated for one hour in N₂ at 540° C. and then it is treated in air for 6 hours at 540° C. The roasted solid contains 10% by weight of TiO₂.

The X-ray diffraction diagram of the roasted product shows the characteristic peak corresponding to a spacing of 29 Å (FIG. 1.) The IR spectrum showed the characteristic band at 960 cm⁻¹.

Example 2

Obtaining MCM-41-Ti with a Si/Ti ratio higher than that shown in example 1

One prepares 110 g of an aqueous solution that contains 11.6% CTMAOH and 17.3% CTMABr. To this, an aqueous solution of tetramethylammonium silicate prepared according to example 1 is added with continuous stirring and at room temperature. After perfect homogenization 11.85 g of SiO₂ (Aerosil 200©) are added and finally (C₂H₅O) ₄Ti is added as the titanium source, in such a way that the synthesis gel has the following molar ratios:

$$\frac{Si}{Ti} = 60; \frac{(CTMA)_2O}{(TMA)_2O} = 0.563; \frac{(TMA)_2O}{SiO_2} = 0.155 = \frac{H_2O}{(TMA)_2O} = 157$$

The synthesis gel was heat in an autoclave, statically, at 140° C. for 28 hours. The yield obtained was 20%. The filtered, washed and dried solid was treated at 540° C. for 1 h in a N₂ atmosphere and 6 hours in air. The roated solid contains 2.3% by weight of TiO₂. The X-ray diffraction diagram has a characteristic spectrum of the MCM-41 structure. The IR spectrum showed the characteristic band at 960 cm⁻¹ (FIG. 2) and the RD-UV spectroscopy showed a band between 200 and 220 nm that indicates the presence of Ti (IV) in the lattice (FIG. 3.) The surface area of the material was 936 m² g⁻¹.

Example 3

Preparation of a sample of MCM-41-Ti containing Al in the lattice 80 g of an aqueous solution that contains 11.5% CTMAOH and 17.3% CTMABR were prepared, to which a solution of tetramethylalmmonium silicate prepared according to example 1 is added, while stirring at room temperature is maintained. After perfect homogenization, 10.64 g of $SiO_2$ (Aerosil 200c) and 0.045 g of $Al_2O_3$ in the form of a hydrated alumina (Catapal B© of Vista Chemical Company®) are added and Ti is added from $(C_2H_5O)_4Ti$, so that the resulting gel has the following composition:

$$\frac{Si}{Ti} = 60; \frac{SiO_2}{Al_2O_3} = 400; \frac{(CMTA)_2O}{(TMA)_2O} =$$

$$0.563; \frac{(TMA)_2O}{SiO_2} = 0.155 = \frac{H_2O}{(TMA)_2O} = 157$$

The gel is crystallized in an autoclave at 137° C. for 109.5 h. The product obtained was filtered, washed, dried and roasted in the conditions described in examples 1,2.

The roasted solid with a content of 0.37% and 2.16% by weight of $Al_2O_3$ and $TiO_2$ respectively, had the X-ray diffraction diagram characteristic of MCM-41. The infrared spectrum showed the band of 960 $cm^{-1}$ and the diffuse refraction spectrum showed a wide band at 200–220 nm that indicates the presence of Ti(V) and in the lattice.

Example 4

Utilization of MCM-41-Ti as a catalyst for oxidation of-1-hexene 2.83 g of 1-hexene (Aldrich®), 0.257 g. of $H_2O_2$ (Dauser®), aqueous solution 35%), 23.57 g of methanol (Merck®) and 0.200 g. of MCM-41-Ti obtained according to example 1 are introduced in a glass reactor, while the reactor is agitated. The reaction temperature was 56° C. After 6 hours the conversion regarding the $H_2O_2$ was 95.1%, with a 75% selectivity.

Example 5

Utilization of MCM-41-Ti as a catalyst for the oxidation of 1-hexene

With the material prepared in example 2, oxidation of 1-hexene was carried out under the same conditions as in example 4. After 6 hours of reaction the conversion of hydrogen peroxide was 75% with an 80% selectivity. The oxidation products of the olefin were 80% epoxide, 8% glycol and 12% of the corresponding esters.

Example 6

Utilization of MCM-41-Ti as a catalyst for the oxidation of cyclododecene

With the sample of catalyst obtained in example 2, oxidation of cyclododecene was carried out in the following conditions: 5.45 g of cyclododecene, 23.57 g of ethanol, 0.822 g of $H_2O_2$ 35% and 0.200 g. of MCM-41-Ti were introduced in a glass reactor. The reaction was carried out at 80° C. Under these conditions the conversion of $H_2O_2$ into oxidation products of cyclododecene was 24.3% after 6 hours of fraction, the epoxide selectivity being 93.4%

Example 7

Results obtained in the oxidation of 1-hexene with a catalyst prepared according to example 3 and in the experimental conditions of example 4

Under these conditions, the conversion into $H_2O_2$ after 6.5 hours was 80.2% with a selectivity to oxygenated products of 1-hexene of 75.1%. The distribution of products corresponded to 65% epoxide, 15% glycol and 20% of the corresponding esters.

Ordinates: Intensity I (counts), arbitrary scale Abscissae: Angle 2θ (degrees)

Figure 1:
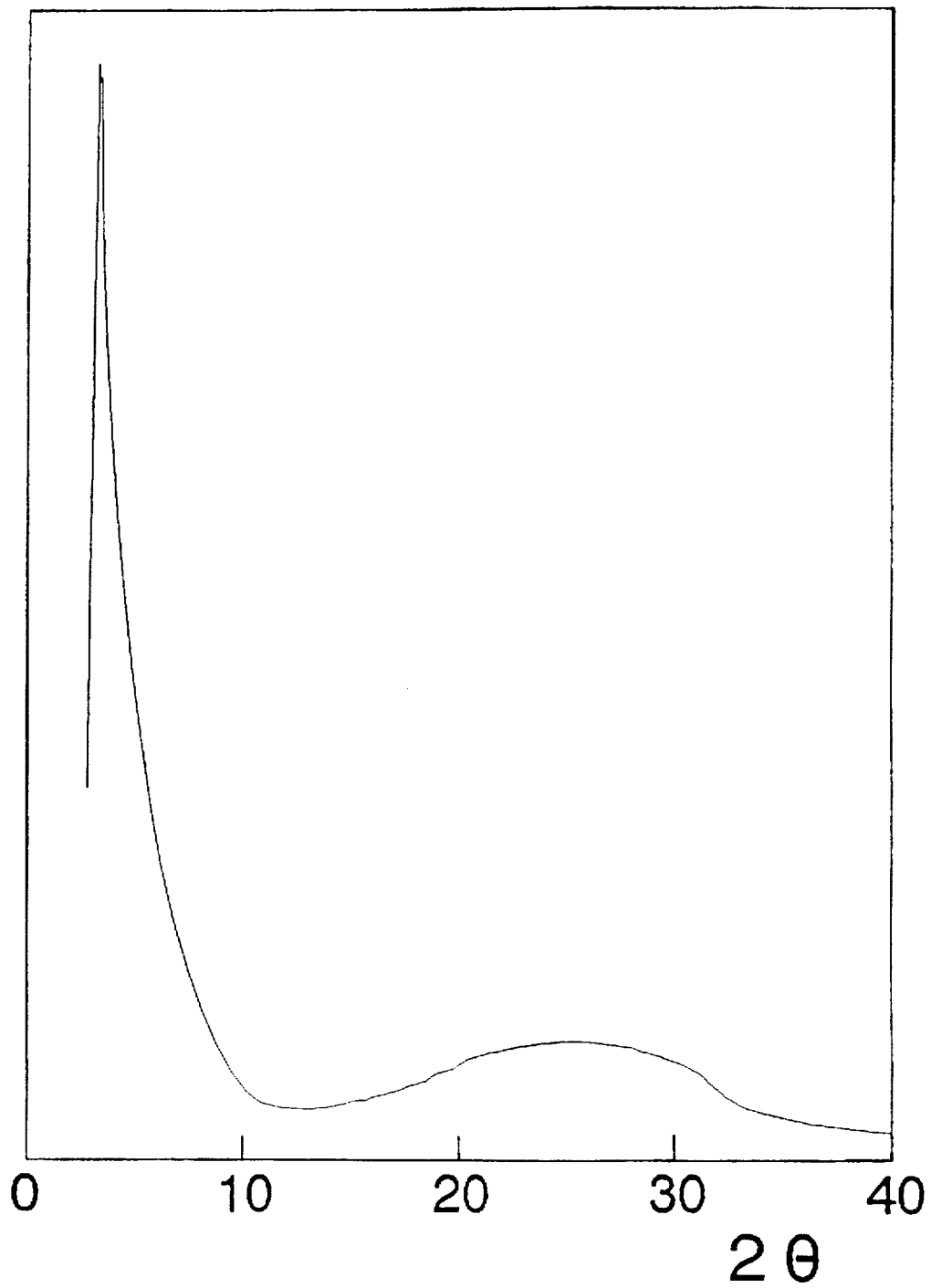
FIG. 1 represents the diffraction diagram of the roasted product of example 1.
Figure 2:
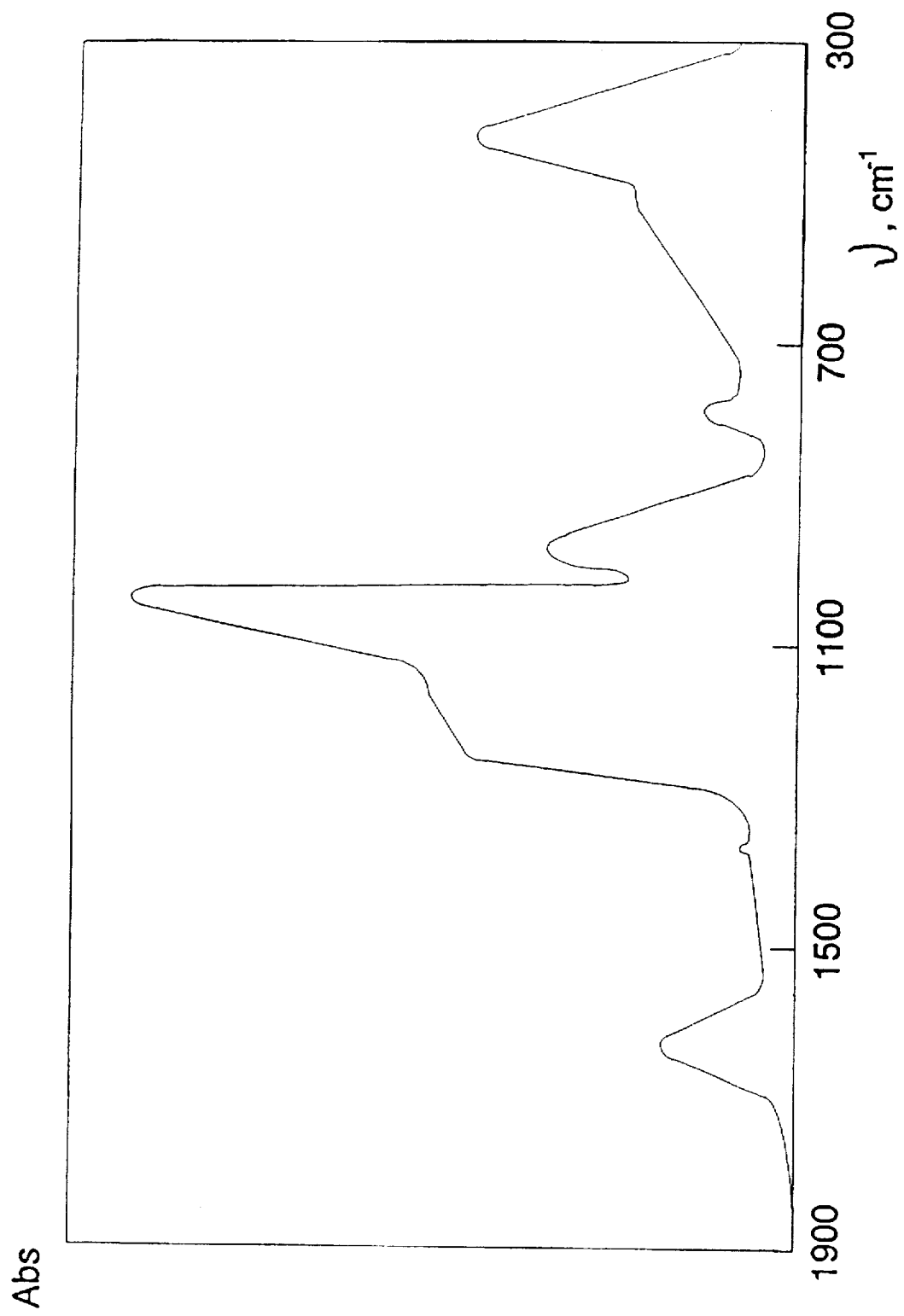

FIG. 2 represents the IR spectrum of the roasted product of example 2.

Ordinates: Absorbance, Abs (u.a.)

Abscissae: Number of waves:y ($cm^{-1}$)

Figure 3:
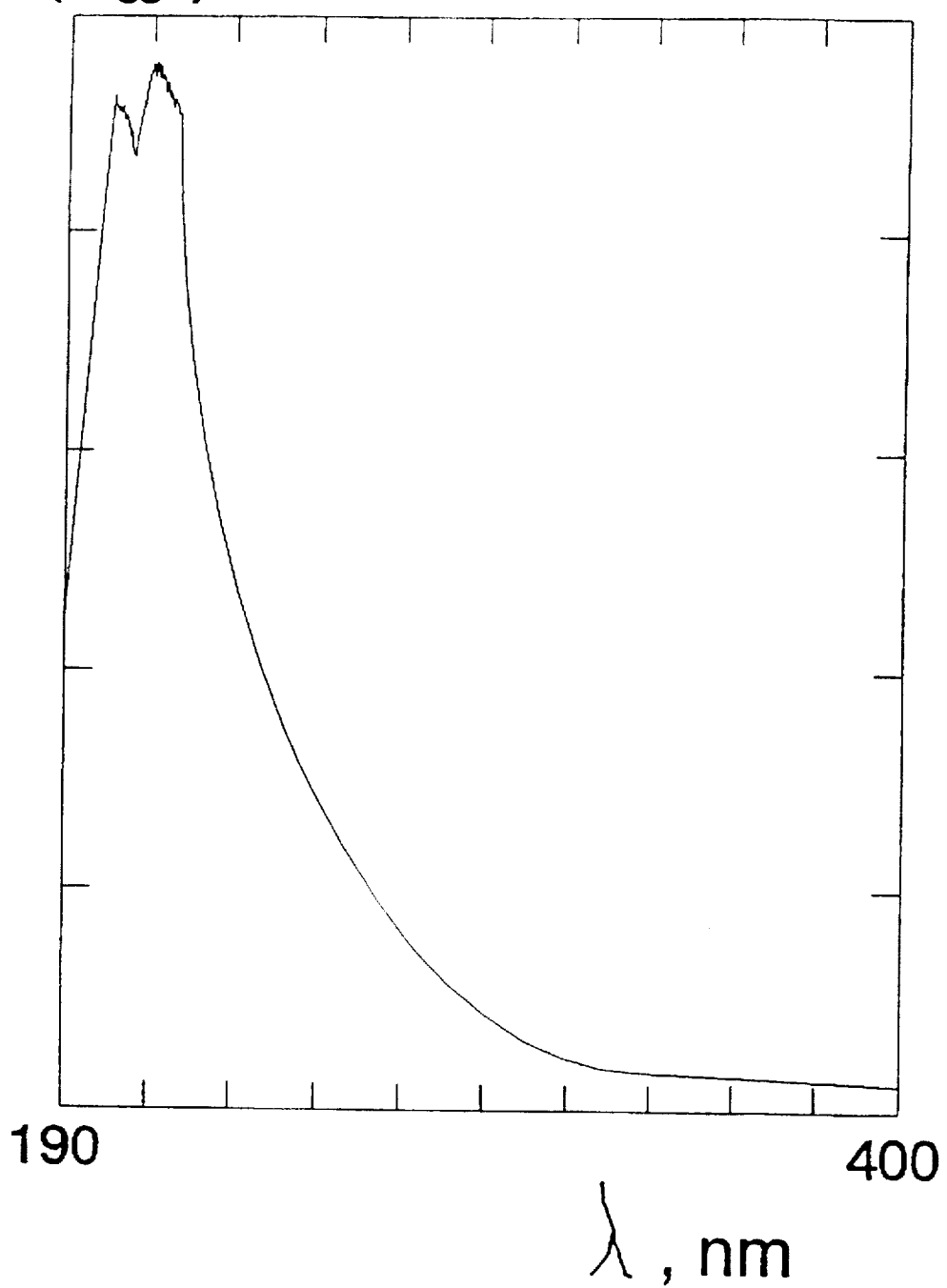

FIG. 3 represents the diffuse refractance spectrum, in the area of the visible ultraviolet (RD-UV) of the roasted product of example 2.

Ordinates: Diffuse refractance, $F(R_{OO})$ (u.a.)

Abscissae: Wave length, λ (nm)

What is claimed:

1. A material for use in selective oxidation of organic products, said material comprising:

a non-pillared crystalline phase having at least one x-ray diffraction peak at a d-spacing of greater that 18 Å and having ultralarge pores and a lattice composed of silicon and titanium oxides, the porosity of the material being greater than 0.2 $cm^3g$, the pores having a diameter larger than 10 Å and less than 200 Å, the material having an intense infrared spectral band at 960±5 $cm^{-1}$ indicating the inclusion of titanium in the lattice;

wherein the material, in anhydrous roasted form, has a composition with the formula:

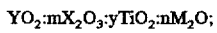

$YO_2:mX_2O_3:yTiO_2:nM_2O$;

wherein:

$YO_2$ is an oxide in which Y represents one or more cation with a valence of 4, consisting of Si and optionally Ge cations;

$X_2O_3$ is an oxide wherein X represents one or more cation with a valence of 3 selected from the group consisting of Al, Ga and B cations;

$M_2O$ is an oxide wherein M represents one or more ion-exchangeable cations selected from the group consisting of $Na^+$, $K^+$ and $H^+$;

m, y and n represent molar proportions of corresponding oxides with regard to $YO_2$, wherein m≦0.1; $10^{-4}$≦y≦0.2; and n≦0.1.

2. A method of making the material of claim 1, comprising:

in a first step, adding a second solution to a first solution to form a first mixture, the first solution being an aqueous or alcohol or hydroalcohol solution of a quaternary ammonium ion, said quaternary ammonium ion being in hydroxide or halide form, said second solution being an aqueous or alcohol or hydroalcohol solution of tetramethylammonium silicate;

in a second step, stirring said first mixture until the first mixture is homogeneous;

in a third step, adding to the first mixture a Ti source and then hydrolyzing said Ti source whereby a first gel is obtained;

in a fourth step, heating said first gel to a first temperature, said first temperature being a temperature between 60° C. and 200° C., for a first period, said first period being a period of between 2 and 180 hours, whereby a first product is obtained;

in a fifth step, washing said product, thereafter drying said product, and thereafter roasting said product at a temperature higher than 400° C.

3. The method of claim 2, wherein the quaternary ammonium ion of the first solution is in hydroxide form.

4. The method of claim 2, wherein the quaternary ammonium ion is in halide form.

5. The method of claim 2, wherein the Ti source is a Ti alkoxide.

6. The method of claim 2, wherein the third step further comprises, prior to adding the Ti source, adding to the first mixture and hydrolyzing an X source.

7. The method of claim 6, wherein the X source is selected from the group consisting of $Al_2O_3$ and $Al(NO_3)_3$ and wherein X is hydrolyzed using an alkaline hydroxide.

8. The method of claim 7, wherein the alkali metal hydroxide is sodium hydroxide.

9. The method of claim 2, wherein the third step further comprises adding to the first mixture a solution of a $Na^+$ salt.

10. The method of claim 9, wherein the $Na^+$ salt is NaCl.

11. The method of claim 2, wherein the third step further comprises the step of adding to the first mixture, a solution of a $K^+$ salt.

12. The method of claim 11, wherein the $K^+$ salt is KCl.

13. The method of claim 2, wherein the first temperature is a temperature between 80° C. and 180° C.

14. The method of claim 2, wherein said first period is a period of between 5 and 140 hours.

15. The method of claim 2, wherein the quaternary ammonium ion has the formula $NR_1R_2R_3R_4^+$ wherein $R_2$, $R_3$ and $R_4$ are independently organic groups with a chain length of from 1 to 6 carbon atoms; and $R_1$ is an organic group comprising saturated or unsaturated chains.

16. The method of claim 2, wherein the quaternary ammonium ion is partly in hydroxide form and partly in halide form, and wherein the molar proportion of halide to $OH^-$ is between 0 and 20.

17. The method of claim 16, wherein the molar proportion of halide to $OH^-$ is approximately ½.

18. The method of claim 15, wherein $R_2$, $R_3$, and $R_4$ are $CH_3$.

19. The method of claim 15, wherein $R_1$ has a linear or branched aliphatic chain, said chain comprising from 2 to 36 carbon atoms.

20. The method of claim 19, wherein said chain comprises from 10 to 18 carbon atoms.

21. The method of claim 15, wherein the quaternary ammonium ion is selected from the group consisting of hexadecylpyridinum, dodecyltrimethylammonium, benzyltrimethylammonium, dimethyldidodecylamonium, hexadecyltrimethylammonium and hexadecyltrimethylphosphonium cations.

22. The method of claim 2, comprising adding to the first mixture, after stirring, silica in the proportion of 0.18 to 1.8 moles per liter of the mixture and titanium source so as to obtain a $TiO_2/SiO_2$ ratio of between $10^{-4}$ and 0.2.

23. The method of claim 22, wherein the titanium is added as tetraethylalkoxide $(C_2H_5O)_4Ti$.

24. The method of claim 2, wherein the first solution is an aqueous solution and the second solution is an aqueous solution.

25. The method of claim 2, wherein the first solution is an alcohol solution and the second solution is an alcohol solution.

26. The method of claim 25, wherein the alcohol has a linear chain.

27. The method of claim 25, wherein the alcohol has a branched chain.

28. The method of any of claim 25, wherein the alcohol has a chain comprising from 1 to 16 carbon atoms.

29. The method of claim 2, wherein the first solution is a hydroalcohol solution; and the second solution is a hydroalcohol solution.

\* \* \* \* \*